United States Patent
Mull et al.

(10) Patent No.: US 8,586,145 B2
(45) Date of Patent: Nov. 19, 2013

(54) METHOD AND TREATMENT COMPOSITION FOR IMPARTING DURABLE ANTIMICROBIAL PROPERTIES TO CARPET

(75) Inventors: Todd Mull, Ringgold, GA (US); James Lesslie, Dalton, GA (US); Danny S. Wade, Cohutta, GA (US)

(73) Assignee: Beaulieu Group, LLC, Dalton, GA (US)

(*) Notice: Subject to any disclaimer, the term of this patent is extended or adjusted under 35 U.S.C. 154(b) by 851 days.

(21) Appl. No.: 12/683,914

(22) Filed: Jan. 7, 2010

(65) Prior Publication Data

US 2010/0173121 A1 Jul. 8, 2010

Related U.S. Application Data

(60) Provisional application No. 61/143,108, filed on Jan. 7, 2009.

(51) Int. Cl.
*B05D 3/02* (2006.01)
*B05D 3/04* (2006.01)

(52) U.S. Cl.
USPC ........ 427/377; 427/389.9; 427/394; 427/352; 427/354; 427/393.4

(58) Field of Classification Search
USPC .............. 427/377, 331, 389.9, 394, 352, 354, 427/385.5, 393.4; 428/96; 442/79, 80, 82, 442/86, 88, 91, 92
See application file for complete search history.

(56) References Cited

U.S. PATENT DOCUMENTS

| | | | |
|---|---|---|---|
| 4,076,631 A * | 2/1978 | Caruso et al. | 252/8.61 |
| 5,527,582 A | 6/1996 | Callebert | |
| 5,762,650 A * | 6/1998 | Ruggiero et al. | 8/490 |
| 6,197,378 B1 * | 3/2001 | Clark et al. | 427/315 |
| 6,294,589 B1 * | 9/2001 | Moody | 521/76 |
| 6,379,686 B1 * | 4/2002 | Harris et al. | 424/405 |
| 6,463,963 B1 * | 10/2002 | Moody et al. | 139/420 R |
| 6,472,019 B1 * | 10/2002 | Yamaguchi et al. | 427/354 |
| 6,524,492 B2 * | 2/2003 | Williams et al. | 252/8.62 |
| 6,613,862 B2 * | 9/2003 | Clark et al. | 528/49 |
| 6,740,357 B2 * | 5/2004 | Yamaguchi et al. | 427/352 |

(Continued)

FOREIGN PATENT DOCUMENTS

| | | |
|---|---|---|
| EP | 0475434 A2 | 3/1992 |
| JP | 9170154 A | 6/1997 |

(Continued)

OTHER PUBLICATIONS

Abstract—Database WPI Week 199736, 1997-389669, Jun. 30, 1997, XP002573321, Thomson Scientific, London, United Kingdom.

(Continued)

*Primary Examiner* — Cheryl Juska
(74) *Attorney, Agent, or Firm* — Sutherland Asbill & Brennan LLP

(57) ABSTRACT

Methods and treatment compositions for imparting durable antimicrobial properties to carpet are provided. The method includes applying a composition comprising a first antimicrobial compound and a fluoropolymer to the carpet substrate. The carpet substrate may be steamed thereafter. The treatment composition may comprise a fluoropolymer, an antimicrobial compound selected from a group consisting of zinc pyrithione, a silver-containing antimicrobial compound and combinations thereof, and a foamer. Carpet products treated with the treatment composition or treated in accordance with the methods are also provided.

16 Claims, 1 Drawing Sheet

(56) References Cited

U.S. PATENT DOCUMENTS

| | | | |
|---|---|---|---|
| 6,818,253 B2* | 11/2004 | Kimbrell | 427/393.4 |
| 6,833,082 B2* | 12/2004 | Yamaguchi et al. | 252/8.61 |
| 6,939,580 B2* | 9/2005 | Enomoto et al. | 427/354 |
| 7,147,669 B2* | 12/2006 | Yamaguchi et al. | 8/115.51 |
| 7,157,121 B2* | 1/2007 | Jones, Jr. | 427/412 |
| 7,247,352 B2* | 7/2007 | Jones, Jr. | 427/412 |
| 7,311,959 B2* | 12/2007 | Jones, Jr. | 428/96 |
| 7,524,551 B2* | 4/2009 | Fang et al. | 428/196 |
| 7,678,155 B2* | 3/2010 | Yamamoto et al. | 8/115.6 |
| 7,717,963 B2* | 5/2010 | Yamaguchi et al. | 8/115.51 |
| 7,758,656 B2* | 7/2010 | Enomoto et al. | 8/115.6 |
| 7,785,437 B2* | 8/2010 | Gilder et al. | 156/250 |
| 7,875,343 B2* | 1/2011 | Gilder et al. | 428/317.1 |
| 8,057,693 B1* | 11/2011 | Ford et al. | 252/8.62 |
| 8,178,119 B2* | 5/2012 | Stutte et al. | 424/411 |
| 2001/0005530 A1 | 6/2001 | Clark et al. | 427/393.4 |
| 2002/0151644 A1* | 10/2002 | Williams et al. | 524/801 |
| 2002/0189023 A1* | 12/2002 | Yamaguchi et al. | 8/115.51 |
| 2003/0051294 A1* | 3/2003 | Yamaguchi et al. | 8/115.51 |
| 2003/0096545 A1* | 5/2003 | Payne | 442/123 |
| 2003/0106161 A1* | 6/2003 | Enomoto et al. | 8/115.51 |
| 2003/0115678 A1* | 6/2003 | Enomoto et al. | 8/115.51 |
| 2003/0157256 A1* | 8/2003 | Yamaguchi et al. | 427/378 |
| 2003/0161953 A1* | 8/2003 | Enomoto et al. | 427/337 |
| 2003/0203153 A1* | 10/2003 | Jones, Jr. | 428/95 |
| 2004/0202816 A1* | 10/2004 | Jones, Jr. | 428/95 |
| 2004/0202818 A1* | 10/2004 | Yamamoto et al. | 428/96 |
| 2005/0175811 A1* | 8/2005 | Kubota et al. | 428/96 |
| 2006/0281851 A1 | 12/2006 | Salsman | |
| 2007/0000106 A1* | 1/2007 | Jones, Jr. | 28/100 |
| 2007/0028395 A1* | 2/2007 | Yamaguchi et al. | 8/115.51 |
| 2008/0139063 A1* | 6/2008 | Fang et al. | 442/94 |
| 2008/0196813 A1 | 8/2008 | Doney et al. | |
| 2008/0236443 A1 | 10/2008 | Salsman | |
| 2008/0260860 A1* | 10/2008 | Stutte et al. | 424/641 |
| 2009/0022936 A1 | 1/2009 | McGill | |
| 2009/0087612 A1 | 4/2009 | Salsman | |
| 2009/0256103 A1* | 10/2009 | Saif et al. | 252/8.62 |
| 2010/0129594 A1* | 5/2010 | Yamaguchi et al. | 428/96 |
| 2010/0143641 A1* | 6/2010 | Yamamoto et al. | 428/96 |
| 2010/0173120 A1 | 7/2010 | McGill | |
| 2010/0316835 A1* | 12/2010 | Nakamura et al. | 428/96 |
| 2011/0020591 A1* | 1/2011 | Nakamura et al. | 428/96 |

FOREIGN PATENT DOCUMENTS

| | | | |
|---|---|---|---|
| JP | 11217745 A * | 8/1999 | |
| WO | 9014107 A1 | 11/1990 | |
| WO | 9314927 A1 | 8/1993 | |
| WO | 9837981 A1 | 9/1998 | |
| WO | 02102582 A2 | 12/2002 | |
| WO | WO 2008046746 A2 * | 4/2008 | |

OTHER PUBLICATIONS

International Search Report and Written Opinion (PCT/US2010/020438), International Searching Authority.

* cited by examiner

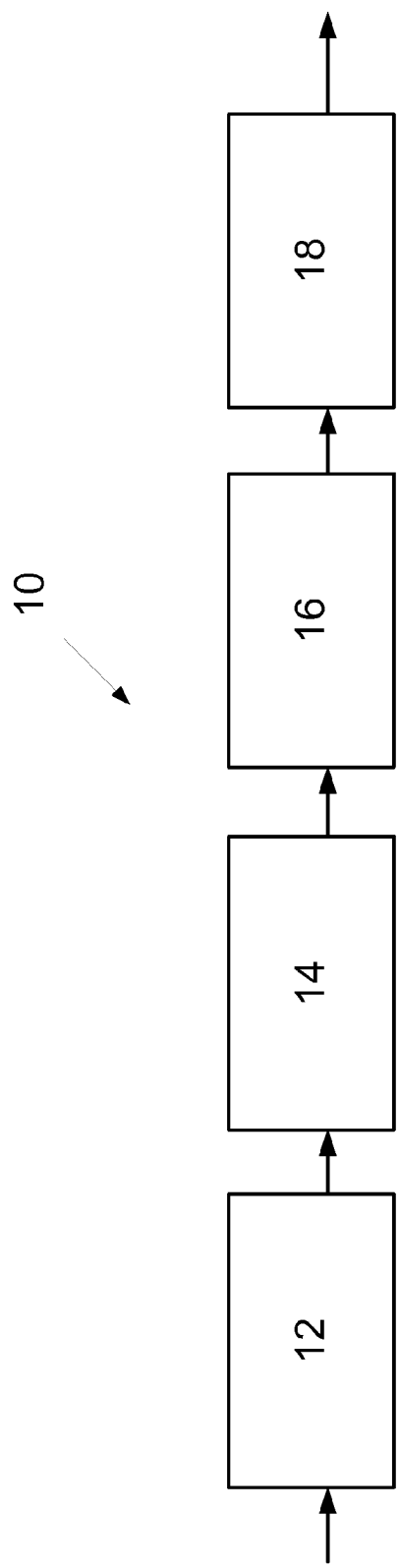

METHOD AND TREATMENT COMPOSITION FOR IMPARTING DURABLE ANTIMICROBIAL PROPERTIES TO CARPET

CROSS REFERENCE TO RELATED APPLICATIONS

This application claims priority under 35 U.S.C. §119(e) to U.S. Provisional Patent Application Ser. No. 61/143,108, filed on Jan. 7, 2009, which is incorporated herein by reference in its entirety.

STATEMENT REGARDING FEDERALLY SPONSORED RESEARCH OR DEVELOPMENT

Not applicable.

BACKGROUND OF THE INVENTION

This invention relates generally to the field of carpets, and more particularly to carpets having antimicrobial properties.

Various antimicrobial treatments are currently used in the carpet industry to impart antimicrobial properties to the manufactured carpet. The most popular methods include topical applications and dry cure applications of antimicrobial compounds to the carpet substrate. However, conventional antimicrobial treatment methods used in the industry have damaging effects on carpet performance attributes such flame resistance, soil resistance, and color fastness. For example, many antimicrobial compounds, when applied topically to a carpet substrate following a fluoropolymer treatment and prior to drying in a dryer, will increase the flammability of the carpet.

BRIEF SUMMARY OF THE INVENTION

In one aspect, a method of treating a carpet substrate is provided. The method may include applying a composition comprising a first antimicrobial compound and a fluoropolymer to the carpet substrate.

In another aspect, a method of treating a carpet substrate is provided that comprises applying a first antimicrobial compound and a fluoropolymer to the carpet substrate, and thereafter steaming the carpet substrate.

In another aspect, a treatment composition is provided for imparting durable antimicrobial properties to a carpet. The treatment composition may comprise a fluoropolymer; an antimicrobial compound selected from a group consisting of zinc pyrithione, a silver-containing antimicrobial compound and combinations thereof; and a foamer.

Carpet products treated with the treatment composition or treated in accordance with the methods are also provided.

BRIEF DESCRIPTION OF THE DRAWINGS

FIG. 1 is a diagram, illustrating a method of imparting durable antimicrobial properties to a carpet in accordance with one or more embodiments of the present invention.

DETAILED DESCRIPTION OF THE INVENTION

Methods have been developed to provide a carpet with durable antimicrobial properties using modern continuous application equipment without negating or diminishing other desirable performance characteristics of the carpet. The present method can impart antimicrobial properties to a variety of carpet materials comprising various types of fibers including, but not limited to, nylon, polyester, wool, polypropylene, PTT, silk, cotton, rayon, acetate, and combinations thereof.

It has been discovered that durable antimicrobial properties may be imparted to a carpet in a continuous, single-step treatment with a fluoropolymer without diminishing combined performance attributes. In one embodiment, one or more antimicrobial compounds are applied via foam in an exhaust application step utilizing a foam applicator such as a Küsters Fluicon™ foam applicator (Andritz Küsters GmbH) immediately before feeding the carpet into a steamer. Once the carpet exits the steamer, it typically is washed and extracted prior to entrance into the dryer.

One embodiment of the method is illustrated in FIG. 1. The treatment process 10 may be readily integrated with a continuous manufacturing process which feeds a carpet substrate through various in-line process equipment, such as is known in the art. In treatment process 10, the carpet substrate may be first fed through a treatment apparatus 12, then immediately through a steamer 14, then through a washing apparatus 16 and a dryer 18. In the treatment apparatus 12, the carpet substrate may be subjected to foam treatment with a foam comprising one or more suitable antimicrobial compounds and a fluoropolymer. Various antimicrobial compounds may be used including, but not limited to, Ultrafresh™ DM-50, commercially available from Thompson Research Associates (Canada), Alphasan™ RC-5000, commercially available from Milliken Chemical (Spartanburg, S.C.), Zinc Omadine™ and Reputex™ 20, commercially available from Arch Chemical (Norwalk, Conn.). In one embodiment, the antimicrobial compound is zinc pyrithione and/or AlphaSan™, which is an antimicrobial compound available from Milliken Chemicals (Spartanburg, S.C.). Alphasan is believed to be a zirconium phosphate-based ceramic ion-exchange resin containing silver.

In a preferred embodiment, a treatment composition is applied to the carpet substrate. The treatment composition may be in the form of a foam and may comprise a fluoropolymer, a foamer, magnesium sulfate liquid, zinc pyrithione, and a zirconium phosphate-based ceramic ion-exchange resin containing silver. Various fluoropolymers may be used including, but not limited to, Centapel EFP-7, commercially available from Centaur Technologies (Dalton, Ga.), Unidyne™ TG 580, TG 581, TG 2211 and TG 2511, all of which are commercially available from Daikin America, Inc. (Orangeburg, N.Y.); PM 1396, PM 1399, PM 1400 and PM 1451, all of which are commercially available from 3M Specialty Chemicals Division (St. Paul, Minn.); Capstone™ RCP and Capstone™ TUC, both of which are commercially available from DuPont (Wilmington, Del.). In some embodiments, an aqueous composition of the treatment composition contains 3M PM 1399 which is commercially available from 3M Innovative Products (Minneapolis, Minn.). The fluoropolymer may be provided in an amount of about 0.05 to about 20% owg (on the weight of the goods), or about 0.4% owg. The magnesium sulfate liquid may be provided in an amount of about 0.1 to about 20% owg, or about 2.0% owg.

Various foamers may be used including, but not limited to, Centafoam YEP-10, which is available from Centaur Technologies. The foamer may comprise about 0.1 to about 100 g/l of the treatment composition or about 4.0 g/l of the treatment composition. The treatment may also comprise Centafresh, which is available from Centaur Technologies, in an amount of about 7 g/sq. yd. of carpet substrate. The treatment composition may also comprise various pH adjusting additives such as System 404, which is available from Phoenix Chemical (Calhoun, Ga.). The pH of the treatment composition may be about 2.0 to about 12.0, or about 2.1.

The treatment composition may comprise various antimicrobial compositions including, but not limited to, zinc pyrithione and silver-containing antimicrobial compounds. The zinc pyrithione may comprise about 1 to about 50,000 ppm of the treatment composition or about 500 ppm of the treatment composition. Various silver-containing antimicrobial compounds may be used including Alphasan, which is available from Milliken Chemicals (Spartanburg, S.C.). The silver-containing antimicrobial compound may comprise about 1 to about 50,000 ppm of the treatment composition or about 200 ppm of the treatment composition.

In one embodiment, after the carpet substrate is treated with the fluoropolymer and antimicrobial compound composition, the carpet substrate is immediately steamed in the steamer 14. The carpet substrate is then rinsed and extracted by the washing apparatus 16 and dried in the dryer 18.

It has been observed that treating the carpet substrate with a fluoropolymer and an antimicrobial compound in a single stage results in unexpected synergistic effects and improved performance properties. In particular, the treated carpet demonstrates durable antimicrobial properties, excellent stain repellency and color fastness without diminished flame resistance.

EXAMPLES

In each of the following examples tufted filament polyester carpet dyed with disperse dyes were from Beaulieu of America (Chatsworth, Ga.) were used for the sample carpet substrates.

The following chemicals were also used in the examples: Zinc Pyrithione, an antimicrobial compound available from Arch Chemicals (Norwalk, Conn.); Alphasan, a silver containing antimicrobial compound available from Milliken Chemicals (Spartanburg, S.C.); Invasan RCD, a sugar-derived freshener available from Huntsman Textile Effects (Switzerland); Centafresh, available from Centaur Technologies; PM 1399, a fluoropolymer available from 3M Innovative Products (Minneapolis, Minn.); Centafoam YEP-10, a foamer available from Centaur Technologies; Centex Binder, a binding agent available from Centaur Technologies; System 404, available from Phoenix Chemical (Calhoun, Ga.); and magnesium sulfate liquid.

Example One

A foam was prepared containing 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to a polyester filament carpet at 100% wet pick up. The carpet was then subjected to steam for 60 seconds then rinsed and extracted prior to entrance into the dryer.

Example Two

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and then the carpet was subjected to steam for 60 seconds then rinsed and extracted.

After extraction the carpet was treated with the second step. The second step was an 8% wet pick up topical foam application. The solution used in the second step contained Alphasan at 1000 ppm with Centafoam YEP-10 at 4.0 g/l. The solution was applied to the fiber by topical foam and then the carpet was placed into an oven at 140 degrees C. until dry.

Example Three

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and subjected to steam for 60 seconds then rinsed and extracted.

After extraction the carpet was treated with the second step. The second step was an 8% wet pick up topical foam application. The solution used in the second step contained Alphasan at 1000 ppm with 0.5% owg Centex Binder and Centafoam YEP-10 at 4.0 g/l. The solution was applied to the fiber by topical foam and then the carpet was placed into an oven at 140 degrees C. until dry.

Example Four

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and then the carpet was subjected to steam for 60 seconds then rinsed and extracted.

After extraction the carpet was treated with the second step. The second step was an 8% wet pick up topical foam application. The solution used in the second step contained Zinc Pyrithione at 500 ppm and Centafoam YEP-10 at 4.0 g/l. The solution was applied to the fiber by topical foam and the carpet was then placed into an oven at 140 degrees C. until dry.

Example Five

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and the carpet was subjected to steam for 60 seconds then rinsed and extracted.

After extraction the carpet was treated with the second step. The second step was an 8% wet pick up topical foam application. The solution used in the second step contained Zinc Pyrithione at 500 ppm with 0.5% owg Centex Binder and Centafoam YEP-10 at 4.0 g/l. The solution was applied to the fiber by topical foam and the carpet was then placed into an oven at 140 degrees C. until dry.

Example Six

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and the carpet was subjected to steam for 60 seconds then rinsed and extracted.

After extraction the carpet was treated with the second step. The second step was an 8% wet pick up topical foam application. The solution used in the second step contained Invasan at 500 ppm and Centafoam YEP-10 at 4.0 g/l. The solution was applied to the fiber by topical foam and the carpet was then placed into an oven at 140 degrees C. until dry.

Example Seven

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and the carpet was subjected to steam for 60 seconds then rinsed and extracted.

After extraction the carpet was treated with the second step. The second step was an 8% wet pick up topical foam application. The solution used in the second step contained Invasan at 500 ppm with 0.5% owg Centex Binder and Centafoam YEP-10 at 4.0 g/l. The solution was applied to the fiber by topical foam and the carpet was then placed into an oven at 140 degrees C. until dry.

Example Eight

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and the carpet was subjected to steam for 60 seconds then rinsed and extracted.

After extraction the carpet was treated with the second step. The second step was an 8% wet pick up topical foam application. The solution used in the second step contained Alphasan at 200 ppm, Zinc Pyrithione at 500 ppm and Centafoam YEP-10 at 4.0 g/l. The solution was applied to the fiber by topical foam and the carpet was then placed into an oven at 140 degrees C. until dry.

Example Nine

A polyester filament carpet was treated in a two step application process. The first step was an exhaust application at 100% wet pick up via foam. The solution used in the first step contained 3M PM 1399 at 0.4% owg (on the weight of the goods), magnesium sulfate liquid at 2.0% owg, Centafoam YEP-10 at 4.0 g/l, Centafresh at 7 g/sq. yd. The pH of the foam was adjusted to 2.1 with System 404. The foam solution was applied to the fiber and the carpet was subjected to steam for 60 seconds then rinsed and extracted.

After extraction the carpet was treated with the second step. The second step was an 8% wet pick up topical foam application. The solution used in the second step contained Alphasan at 200 ppm, Zinc Pyrithione at 500 ppm with 0.5% owg Centex Binder and Centafoam YEP-10 at 4.0 g/l. The solution was applied to the fiber by topical foam and the carpet was then placed into an oven at 140 degrees C. until dry.

Example Ten

A foam was prepared containing 3M PM 1399 at 0.4% owg (on the weight of the goods), magnesium sulfate liquid at 2.0% owg, Centafoam YEP-10 at 4.0 g/l, Centafresh at 7 g/sq. yd., Alphasan at 200 ppm, Zinc Pyrithione at 500 ppm. The pH of the foam was adjusted to 2.1 with System 404. The foam solution was applied to the carpet and the carpet was subjected to steam for 60 seconds then rinsed and extracted prior to being placed into the dryer.

Example Eleven

A foam was prepared containing 3M PM 1399 at 0.4% owg (on the weight of the goods), magnesium sulfate liquid at 2.0% owg, Centafoam YEP-10 at 4.0 g/l, Centafresh at 7 g/sq. yd., Invasan at 1,000 ppm. The pH of the foam was adjusted to 2.1 with System 404. The foam solution was not applied to the carpet due to coagulation and precipitation.

Example Twelve

A polyester filament carpet sample was maintained non-treated for use as a control.

Example Thirteen

All test samples of EXAMPLES 1-12 were subjected to American Association of Textile Chemists and Colorists (AATCC) test method 138, undergoing 10 cycles wash/extractions. The samples were further subjected to AATCC test method 123, a pill test for flammability, a repellency test, and a 40 hour light fastness test.

TABLE ONE

RESULTS

| Trial # | AATCC 123 Part I | AATCC 123 Part II | AATCC 123 Part III | Pill Test | Repellency | 40 hrs Light Fastness |
|---|---|---|---|---|---|---|
| Example #1 | Fail | Fail | Fail | Pass | Pass | Pass |
| Example #2 | Fail | Fail | Fail | Pass | Pass | Pass |
| Example #3 | Fail | Pass | Fail | Fail | Pass | Pass |
| Example #4 | Fail | Fail | Fail | Pass | Pass | Pass |
| Example #5 | Pass | Pass | Fail | Fail | Pass | Fail |
| Example #6 | Fail | Fail | Fail | Pass | Pass | Pass |
| Example #7 | Fail | Fail | Fail | Fail | Pass | Pass |
| Example #8 | Fail | Fail | Fail | Pass | Pass | Pass |
| Example #9 | Pass | Pass | Fail | Fail | Pass | Fail |
| Example #10 | Pass | Pass | Pass | Pass | Pass | Pass |
| Example #11 | NA | NA | NA | NA | NA | NA |
| Example #12 | Fail | Fail | Fail | Pass | Fail | Pass |

As demonstrated in TABLE ONE, a synergistic effect exists with co-exhaustion of Zinc Pyrithione, Alphasan, Centafresh, PM 1399, and Centafoam YEP-10. Superior results were achieved with this unexpected discovery. Excellent antibacterial/antifungal results, repellency, and light fastness were achieved without causing flammability failures.

Many variations exist for the conditions previously outlined in the examples. Those skilled in the art recognize the many variations for equipment and conditions involving exhaust and topical application of chemical treatments. Previously outlined descriptions are supplied as examples and are not meant to be exclusive.

We claim:

1. A method of treating a carpet substrate comprising:
   preparing a composition comprising zinc pyrithione, a silver-containing antimicrobial compound, a magnesium sulfate liquid, and a fluoropolymer;
   adjusting the pH of the composition to a pH of about 2.0 to about 12.0;
   applying the composition to the carpet substrate in the form of a foam;
   steaming the carpet substrate immediately after application of the composition to the carpet substrate;
   rinsing and extracting the carpet substrate; and
   drying the carpet substrate in a dryer.

2. The method of claim 1, wherein the composition comprises about 1 to about 50,000 ppm zinc pyrithione.

3. The method of claim 1, wherein the composition is applied to the carpet substrate such that the fluoropolymer is applied to the carpet substrate in an amount of about 0.05 to about 20% owg.

4. The method of claim 1, wherein the silver-containing antimicrobial compound comprises a zirconium phosphate-based ceramic ion-exchange resin containing silver.

5. The method of claim 4, wherein the composition comprises from 1 to 50,000 ppm of the zirconium phosphate-based ceramic ion-exchange resin containing silver.

6. The method of claim 5, wherein the composition comprises 200 ppm of the zirconium phosphate-based ion-exchange resin containing silver.

7. The method of claim 1, wherein the composition is applied to the carpet substrate such that the magnesium sulfate liquid is applied to the carpet substrate in an amount of about 0.1 to about 20% owg.

8. The method of claim 7, wherein the magnesium sulfate liquid is applied to the carpet substrate in an amount of about 2.0% owg.

9. The method of claim 1 wherein the composition is applied to the carpet substrate such that the fluoropolymer is applied to the carpet substrate in an amount of about 0.4% owg.

10. The method of claim 1, wherein the composition comprises 500 ppm zinc pyrithione.

11. The method of claim 1, wherein the composition is applied to the carpet substrate via a foam applicator.

12. A method of treating a carpet substrate comprising:
    preparing a composition comprising a fluoropolymer, a magnesium sulfate liquid, zinc pyrithione, a zirconium phosphate-based ceramic ion-exchange resin containing silver, and a pH adjusting additive;
    applying the composition to the carpet substrate in the form of a foam; and thereafter
    steaming the carpet substrate.

13. The method of claim 12, wherein the composition is applied to the carpet substrate such that the fluoropolymer is applied to the carpet substrate in an amount of about 0.05 to about 20% owg.

14. The method of claim 12, wherein the composition comprises from 1 to 50,000 ppm zinc pyrithione.

15. The method of claim 12, wherein the composition has a pH of about 2.1.

16. The method of claim 12, wherein the composition is applied to the carpet substrate via a foam applicator.

* * * * *